United States Patent
Tatara et al.

(10) Patent No.: US 6,316,026 B1
(45) Date of Patent: Nov. 13, 2001

(54) METHOD AND APPARATUS FOR MANUFACTURING TABLET CAPABLE OF QUICK DISINTEGRATION IN ORAL CAVITY

(75) Inventors: Mitsutoshi Tatara; Koji Matsunaga; Toshihito Shimizu, all of Tokyo (JP)

(73) Assignee: Sato Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/227,921

(22) Filed: Jan. 8, 1999

(30) Foreign Application Priority Data

Sep. 22, 1998 (JP) .................................. 10-267789

(51) Int. Cl.⁷ .................. A61K 9/20; A61K 9/28
(52) U.S. Cl. .................. 424/464; 424/465; 424/474; 424/488; 514/777
(58) Field of Search .................. 424/464, 465, 424/474, 441, 439, 440, 484, 488, 469

(56) References Cited

FOREIGN PATENT DOCUMENTS

| | | | |
|---|---|---|---|
| 39 36 112 | 10/1989 | (DE) | A61K/31/54 |
| 0 124 663 | 5/1983 | (EP) | A23L/2/38 |
| 0 636 364 | 7/1994 | (EP) | A61K/9/20 |
| 2 188 915 | 4/1986 | (GB) | A61K/31/54 |
| 8-291051 | 11/1996 | (JP) . | |
| 95/20377 | 8/1995 | (WO) | A61K/9/00 |

*Primary Examiner*—James M. Spear
(74) *Attorney, Agent, or Firm*—Jacobson Holman, PLLC

(57) ABSTRACT

A method and an apparatus are adapted to manufacture a tablet capable of quick disintegration in the oral cavity that has a sufficiently large porosity and can be disintegrated in the oral cavity in a very short period of time, typically between 3 and 5 seconds. A tablet manufactured by means of such a method and such an apparatus also constitutes part of the present invention. The method for manufacturing a tablet capable of quickly disintegration in the oral cavity comprises steps of punching a tablet out of a pharmaceutical composition containing one or more than one medicinal agents and one or more than one water-soluble saccharides under pressure between 0.20 and 0.01 t/cm² and shaping the tablet by moisturizing and drying it, while transferring it without causing it to drop, said tablet having a porosity between 20 and 40%.

6 Claims, 1 Drawing Sheet

METHOD AND APPARATUS FOR MANUFACTURING TABLET CAPABLE OF QUICK DISINTEGRATION IN ORAL CAVITY

BACKGROUND OF THE INVENTION

1. Field of the Invention

In this aging society, there is an increasing need for providing appropriately designed shapes and sizes for medicines to be taken by elderly people without causing any swallowing problem. A poll on the shape and size of medicines good for elderly people conducted recently shows that while tablets are the best choice in terms of easy handling, they are accompanied by a problem of the difficulty of swallowing that elderly people experience because of their weakened ability for deglutition.

Apart from the elderly, there is also a strong demand for medicines that come in different shapes and sizes in order to meet the highly diversified life styles of people in this modern society. For instance, there is a strong demand for medicines that do not require water for swallowing and those infants can take in without difficulty. From this point of view, efforts have been paid recently to develop tablets capable of quickly disintegration in the oral cavity.

This invention relates to a method and an apparatus for manufacturing a tablet capable of quick disintegration in the oral cavity that is adapted to be shaped by a simple process following a punching process.

2. Prior Art

In view of the above identified applications, a tablet of the type under consideration should disintegrate as quickly as possible in the oral cavity once it is orally administered, typically in 15 seconds.

While various methods have been proposed for manufacturing tablets capable of quick disintegration in the oral cavity, any method that requires the use of a specifically designed apparatus entails high manufacturing cost to significantly push up the price of the final product. Additionally, the use of one or more than one particular additives can give rise to problems in terms of the quality and the stability of the produced medicinal products. Therefore, it is preferably that tablets capable of quick disintegration in the oral cavity are made of materials that are popularly used as pharmaceutical excipients and that the method for manufacturing such tablets is very simple.

Japanese Patent Application Laid-Open No. 8-291051 titled as "Method for Manufacturing a Quickly Soluble Tablet and a Tablet Manufactured by such a Method" discloses a process of manufacturing a quickly soluble tablet that comprises three steps of low pressure punching, moisturizing and drying. According to the above patent document, low pressure punching refers to an operation of punching out a tablet with a minimal level of pressure necessary to make it keep its form when moving to the next moisturizing step. The specific pressure level for the punching step described in the patent document is between 0.1 and 2.0 t/cm$^2$, preferably between 0.2 and 1.0 t/c m$^2$. In an example described in the patent document, tablets were punched out under the pressure of 0.3 t/c m$^2$.

According to Japanese Patent Application Laid-Open No. 8-291051, the disclosed method requires the use of a water-soluble binding agent as an indispensable ingredient for making the tablet punched out under low pressure maintain a certain level of hardness.

However, the use of a water-soluble binding agent as described in Japanese Patent Application Laid-Open No. 8-291051 can prolong the time necessary for the tablet to disintegrate in the oral cavity so that the ratio to which the agent is added should be minimized or, if possible, the use of such an agent should be totally avoided.

Additionally, the use of low pressure for punching out a tablet can give rise to a low porosity in the punched out tablet. The void or the fine spaces existing in a tablet normally allow saliva to infiltrate into the inside of the tablet and accelerate the disintegrate of the tablet in the oral cavity. Therefore, the porosity of a tablet that is designed to be capable of quick disintegration in the oral cavity significantly affects the time necessary for the tablet to disintegrate in the oral cavity. The porosity of a tablet produced by a method disclosed in Japanese Patent Application Laid-Open No. 8-291051 and under low punching pressure of 0.1 to 0.2 t/cm$^2$ will be between 20% and 15%. On the other hand, for a tablet to be disintegrated in the oral cavity within 10 seconds, the porosity of the tablet should be not less than 20%, preferably not less than 25%, regardless of the ingredients and the size of the tablet.

SUMMARY OF THE INVENTION

In view of the problems of the known methods for manufacturing a quickly soluble tablet and those of the tablets produced by such methods, it is therefore an object of the present invention to provide a method and an apparatus for manufacturing a tablet capable of quick disintegration in the oral cavity that has a sufficiently large porosity and can be disintegrated in the oral cavity in a very short period of time, typically between 3 and 5 seconds. Another object of the present invention is to provide a tablet manufactured by means of such a method and such an apparatus.

According to a first aspect of the invention, there is provided a method for manufacturing a tablet capable of quick disintegration in the oral cavity, said method comprising steps of punching a tablet out of a pharmaceutical composition containing one or more than one medicinal agents and one or more than one water-soluble saccharides under pressure between 0.20 and 0.1 t/c m$^2$ and shaping the tablet by moisturizing and drying it, while transferring it without causing it to drop, said tablet having a porosity between 20 and 40%.

According to a second aspect of the invention, there is provided an apparatus for manufacturing a tablet capable of quick disintegration in the oral cavity, said apparatus comprising a punching section for punching a tablet out of a medicinal composition containing one or more than one medicinal agents and one or more than one water-soluble saccharides under pressure between 0.20 and 0.20 t/c m$^2$, a transfer unit for transferring the punched out tablet on a continuous basis without causing it to drop, a moisturizing section for moisturizing the punched out tablet being transferred and a drying section arranged downstream relative to said moisturizing section for drying the punched out tablet being transferred, said manufactured tablet having a porosity between 20 and 40%.

According to a third aspect of the invention, there is provided a tablet capable of quick disintegration in the oral cavity and formed by punching it out of a pharmaceutical composition containing one or more than one medicinal agents and one or more than one water-soluble saccharides under pressure between 0.20 and 0.01 t/c m$^2$ and shaping it by moisturizing and drying it, while transferring it without causing it to drop, said tablet having a porosity between 25 and 40%.

In a mode of carrying out the invention, said pharmaceutical composition contains a binding agent to an extent not affecting the time required for the tablet to disintegrate in the oral cavity. In another mode of carrying out the invention, said pharmaceutical composition contains water-soluble saccharides by not lower than 30%. In still another mode of carrying out the invention, said medicinal agents are subjected to a coating process or a process of turning it into a matrix.

DESCRIPTION OF THE PREFERRED MODES OF CARRYING OUT THE INVENTION

Figure 1:
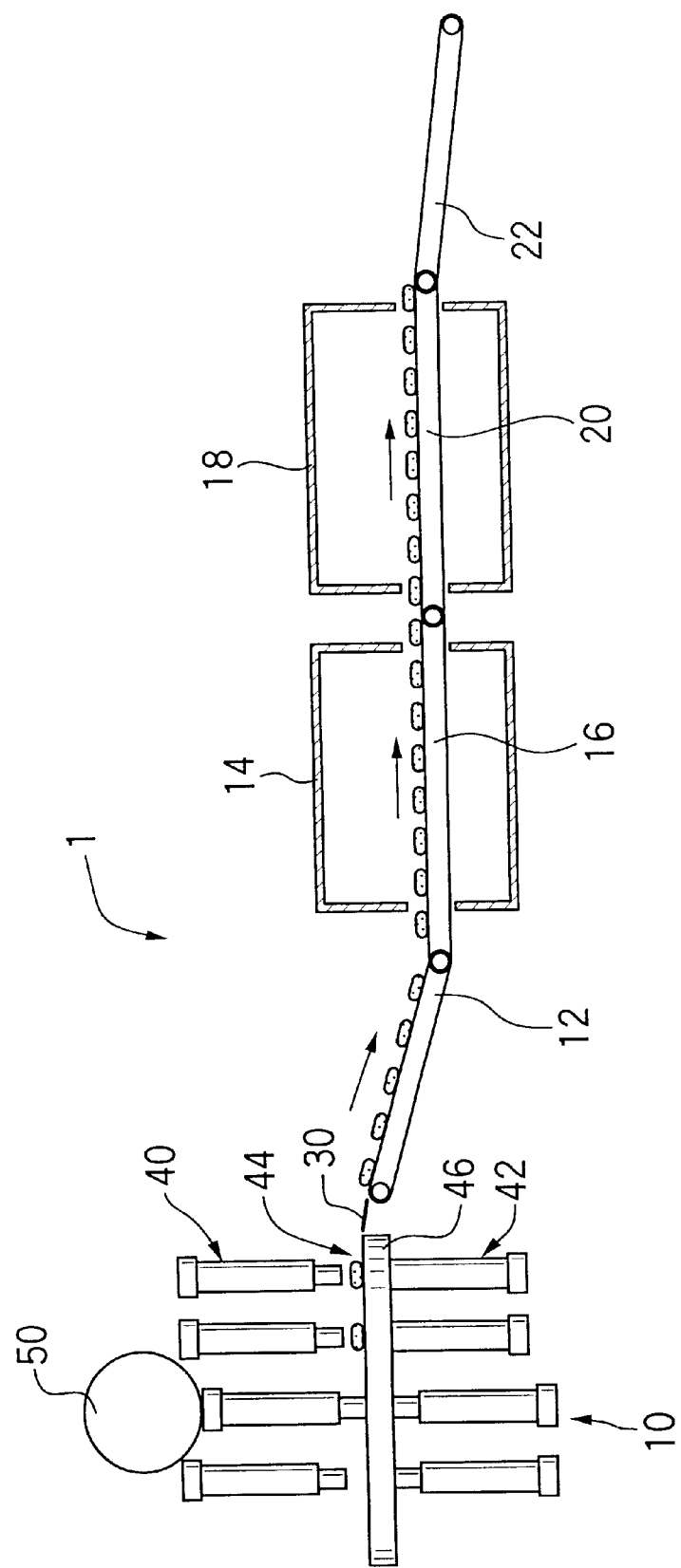
FIG. 1 is a schematic illustration of an embodiment of apparatus for manufacturing a tablet capable of quick disintegration in the oral cavity according to the invention.

Now, an embodiment of apparatus for manufacturing a tablet capable of quick disintegration in the oral cavity according to the invention by referring to the accompanying drawing. Referring to FIG. 1, the manufacturing apparatus 1 comprises a rotary punch-press unit 10, a relay conveyor 12 for transferring one or more than one punched out tablets, a moisturizing conveyor 16 arranged in moisturizing section 14, a drying conveyor 20 arranged in drying section 18 and a delivery conveyor 22. An auxiliary adapter 30 is arranged between the punch-press unit 10 and the relay conveyor 12. A storage container (not shown) is arranged at the front end of the delivery conveyor 22. Each of the conveyors is either of a belt type or of a roller type and made of a material capable of being easily separated from the tablets placed on it, which may be stainless steel or polytetrafluoroethylene, and has a mesh-like structure so that air may vertically pass therethrough to surround the punched out tablets being transferred on it. Preferably, the conveyors are independently driven so that they may be regulated independently for the moving speed.

The rotary punch-press unit 10 includes a plurality of punching sections 44 arranged along the periphery of a rotary disk 46 for punching tablets out of a pharmaceutical composition fed to it by means of respective upper strikers 40 and corresponding lower strikers 42 under a predetermined level of pressure, by a pressure roller 50. The auxiliary adapter 30 receives the punched out tablets from the rotary punch-press unit 10 substantially at the punch-press level and feeds them to the relay conveyor 12 along a sliding slope without causing them to drop.

In the moisturizing section 14, the temperature and the relative humidity in the inside of the section and the moving speed of the moisturizing conveyor 16 will be regulated so that punched out tablets may typically be moisturized at temperature of 45° C. with a relative humidity level of 95% for a moisturizing period of 60 seconds. On the other hand, in the drying section 18, hot air heated to 50° C. may be fed at a rate of 5 m3/min. and the moving speed of the drying conveyor 20 may typically be so regulated as to dry the tablet for 60 seconds.

A microwave type or hot steam type moisturizer will be used in the moisturizing zone and operated so as to uniformly moisturize tablets. Anyway, tablets will be held in a highly wet environment in the moisturizing zone and made to pass through it in a predetermined period of time.

Ventilation, depressurization, the use of microwaves or far-infrared rays or some other drying technique may be employed in the drying zone if such a technique is adequate for drying tablets and making them show a level of hardness good for storage after passing through the drying zone in a predetermined period of time.

Embodiment

The pharmaceutical composition that can be used for the purpose of the invention contains medicinal agents as ingredients to a ratio not greater than 70%, preferably not greater than 30%. Some of such medicinal agents may be added after subjecting the medicinal agents to a coating process or a process of turning it into a matrix in order to mask the bitterness or some other stimulating effect of the medicine or to prevent the water-repelling effect of the medicine that can delay the disintegrate of the tablet. For the purpose of the invention, any technique may be used for the coating process or the process of turning the tablet into a matrix. In other words, an appropriate technique is to be selected depending on the level of bitterness, that of agitation, that of water-repellence and/or the size and the shape of the crystals contained in the composition. However, from the viewpoint of disintegration in the oral cavity, a tablet of a pharmaceutical composition according to the invention contains particles of the medicinal ingredients generally not greater than 500 µm, preferably not greater than 100 µm.

The ratio of the water-soluble saccharides contained in a tablet according to the invention is not less than 30%, preferably not less than 50%, most preferably not less than 70%. While any water-soluble saccharides may be used for the purpose of the invention, the use of sugar alcohols is preferable from the viewpoint of the time required for the tablet to disintegrate in the oral cavity and the cool and fresh feeling they gives out when the tablet disintegrates in the oral cavity. Saccharides that can preferably be used for the purpose of the invention include erythritol, xylitol and mannitol. Any of these water-soluble saccharides may be combined to regulate the disintegration effect, the hardness and the agreeableness of the produced tablet.

The lubricant to be used for a tablet according to the invention is selected from magnesium stearate, calcium stearate, sodium stearate, hydrogenated rapeseed oil, hydrogenated caster oil, sucrose esters of fatty acids, fattey acid esters of glycerol, stearil sodium fumarate, sodium benzoate, L-leucine and L-valine. The ratio to which the lubricant is added is not greater than 2.0%, preferably not greater than 0.5%. It may be added either internally or externally and selected according to the combined stability of the medicinal agents and the lubricant, the sticking effect of the medicinal agents and the expected disintegration effect of the tablet in the oral cavity.

EXAMPLES FOR COMPARISON (1) Formulation A

| | |
|---|---|
| dihydrocodeinephosphate | 10 wt portions |
| erythritol | 975 wt portions |
| aspartame | 10 wt portions |
| magnesium stearyte | 5 wt portions |

The dihydrocodeinephosphate, the erythritol and the aspartame as listed above were mixed and a 180 wt portions of ethanol was added to the mixture. Then, the mixture was put into an extruder to produce granules, which were then dried by blowing air thereto. Thereafter, the magnesium stearyte was added to the granular mixture, which was then continuously subjected to punching, moisturizing and drying steps in a manufacturing apparatus as shown in FIG. 1. The produced tablets were made to show a diameter of 15 mm and weigh 1,000 mg. The pressure used for the punching operation was made to vary between 0.03 and 2.00 t/c m².

In the moisturizing zone of the apparatus, the temperature and the relative humidity were constantly held to 40° C. and 90% respectively and the running speed of the conveyor was regulated to make the tablets pass through the zone in 30 seconds. In the drying zone of the apparatus, on the other hand, 50° C. hot air was made to flow at a rate of 5 m³/min. and the running speed of the conveyor there was regulated to make the tablets pass through the zone in 120 seconds. The tablets moved out of the drying zone were filled in a storage tank and thoroughly dried in a drying chamber.

(2) Formulation B

| | |
|---|---|
| dihydrocodeinephosphate | 10 wt portions |
| erythritol | 955 wt portions |
| aspartame | 10 wt portions |
| P.V.P-K25 | 20 wt portions |
| magnesium stearyte | 5 wt portions |

The dihydrocodeinephosphate, the erythritol and the aspartame as listed above were mixed and then the P.V.P-K25 and a 180 wt portions of ethanol was added to the mixture. Then, the mixture was put into an extruder to produce granules, which were then dried by blowing air thereto. Thereafter, magnesium stearate was added to the granular mixture, which was then subjected to the manufacturing steps same as those described above by referring to the Formulation A.

Evaluation tablet hardness: A rheometer available from Fudo Industries Co., Ltd. was used. 10 tablets were tested and the average was determined.

porosity: The true density of the pharmaceutical composition (Mg/cm3) was determined and then the porosity of the tablet was determined from the volume (Vcm3) and the weight (wg) of the tablet.

$$porosity\ (\%) = \frac{V - \frac{W}{M}}{V} \times 100$$

disintegration time in oral cavity: The time required for each tested tablet to disintegrate in oral cavity was measured by 10 panelists and the average was determined.

Results

| | Formulation A | | | | |
|---|---|---|---|---|---|
| | immediately after punching | | after moisturizing and drying | | |
| punching pressure (t/cm3) | hardness (g) | porosity (%) | hardness (g) | porosity (%) | disintegration time in oral cavity (sec.) |
| 2.00 | 1,350 | 9 | 7,280 | 9 | 49 |
| 1.00 | 870 | 10 | 7,060 | 10 | 41 |
| 0.50 | 210 | 12 | 5,770 | 12 | 17 |
| 0.30 | 80 | 14 | 5,540 | 14 | 10 |
| 0.20 | 20 | 16 | 5,210 | 16 | 8 |
| 0.10 | 10 | 19 | 5,130 | 19 | 7 |
| 0.05 | — | 28 | 5,090 | 28 | 5 |
| 0.03 | — | 35 | 4,940 | 35 | 4 |

It was not possible to measure the hardness of the tablets with punching pressures of 0.05 and 0.03 t/c m² immediately after the punching.

| | Formulation B | | | | |
|---|---|---|---|---|---|
| | immediately after punching | | after moisturizing and drying | | |
| punching pressure (t/cm3) | hardness (g) | porosity (%) | hardness (g) | porosity (%) | disintegration time in oral cavity (sec.) |
| 2.00 | 2,150 | 9 | 7,660 | 9 | 58 |
| 1.00 | 1,040 | 10 | 7,510 | 10 | 47 |
| 0.50 | 380 | 12 | 6,170 | 12 | 20 |
| 0.30 | 150 | 15 | 5,830 | 15 | 11 |
| 0.20 | 70 | 16 | 5,650 | 16 | 10 |
| 0.10 | 40 | 18 | 5,490 | 18 | 8 |
| 0.05 | 20 | 27 | 5,360 | 27 | 6 |
| 0.03 | 20 | 34 | 5,120 | 34 | 4 |

It was not possible to measure the hardness of the tablets with punching pressures of 0.05 and 0.03 t/c m² immediately after the punching.

After the punching, the Formulation A, where binder P.V.P-K25 had not been added, showed a hardness slightly different from that of the formulation B. However, no problem was observed in the manufacturing process because of the use of conveyors for transferring tablets. All the tablets produced by using the Formulation A showed a hardness of not lower than 3,000 g after moisturizing and drying and hence were of high quality.

By applying a punching pressure of 0.05 and 0.03 t/c m², the both formulation A and B produced tablets with a porosity of not lower than 20% and a disintegration time in the oral cavity of not longer than 10 or 5 seconds.

EXAMPLE 1

Antipyretic/Analgesic Tablets for Infants

| Formulation | |
|---|---|
| coated acetaminophen granules: | 55 wt portions |
| acetaminophen: | 50 wt portions |
| refined carnauba wax: | 5 wt portions |
| erythritol: | 160 wt portions |
| mannitol: | 33 wt portions |
| sodium stearyl fumarate: | 2 wt portions |
| total | 250 wt portions |

Manufacturing Process

The erythritol, the mannitol and a 10 weight portions of ethanol were mixed with each other and the mixture as put into an extruder to produce granules, which were then dried by blowing air thereto. Thereafter, the coated acetaminophen granules whose bitterness had been masked by refined-carnauba wax, and the sodium stearyl fumarate, which is a lubricant, were added to the granular mixture, which was then continuously subjected to punching, moisturizing and drying steps in a manufacturing apparatus as shown in FIG. 1. The produced tablets were made to show a diameter of 11 mm and weigh 250 mg. The pressure used for the punching operation was 0.03 t/c m². In the moisturizing zone of the apparatus, the temperature and the relative humidity were constantly held to 45° C. and 95% respectively and the running speed of the conveyor was regulated to make the tablets pass through the zone in 60 seconds. In the drying zone of the apparatus, on the other hand, 50° C. hot air was made to flow at a rate of 5 m³/min. and the running speed of the conveyor there was regulated to make the tablets pass through the zone in 90 seconds. The tablets moved out of the drying zone were filled in a storage tank and thoroughly dried in a drying chamber.

Results

| immediately after punching | | after moisturizing and drying | | |
|---|---|---|---|---|
| hardness (g) | porosity (%) | hardness (g) | porosity (%) | disintegration time in oral cavity (sec.) |
| unmeasurable | 35 | 3,200 | 35 | 5 |

Advantages of the Invention

Thus, according to the invention, it is now possible to manufacture a tablet showing a sufficient porosity and a reduced disintegration time in the oral cavity typically between 3 and 5 seconds.

What is claimed is:

1. A method for manufacturing a tablet capable of quick disintegration in the oral cavity, said method comprising the steps of punching a tablet out of a pharmaceutical composition containing one or more than one medicinal agents and one or more than one water-soluble saccharides without using a water-soluble binding agent under pressure between 0.20 and 0.01 t/c m$^2$ and shaping the tablet by moisturizing and drying it, while transferring it without causing it to drop vertically downward, said tablet having a porosity between 20 and 40%.

2. A method for manufacturing a tablet capable of quick disintegration in the oral cavity according to claim 1, wherein said pharmaceutical composition contains water-soluble saccharides by not lower than 30%.

3. A method for manufacturing a tablet capable of quick disintegration in the oral cavity according to claim 1, wherein said medicinal agents are subjected to a coating process or a process of turning it into a matrix.

4. An apparatus for manufacturing a tablet capable of quick disintegration in the oral cavity, said apparatus comprising a punching section for punching a tablet out of a predetermined pharmaceutical composition consisting essentially of one or more than one medicinal agents and one or more than one water-soluble saccharides with said saccharides not being lower than 30%, said punching taking place under pressure between 0.20 and 0.01 t/c m$^2$, a transfer unit for transferring the punched out tablet on a continuous basis without causing it to drop vertically downward, a moisturizing section for moisturizing the punched out tablet being transferred and a drying section for drying the punched out tablet being transferred so that said resulting manufactured tablet has a porosity of between 20 and 40%.

5. An apparatus for manufacturing a tablet capable of quick disintegration in the oral cavity according to claim 4, wherein said one or more than one medicinal agents are subjected to a coating unit for coating or turning the medicinal agent into a matrix.

6. A method for manufacturing a tablet capable of quick disintegration in the oral cavity, said method comprising the steps of punching a tablet out of a pharmaceutical composition consisting essentially of one or more than one medicinal agents and one or more than one water-soluble saccharides under pressure between 0.20 and 0.01 t/c m$^2$ and shaping the tablet by moisturizing and drying it, while transferring it without causing it to drop, said tablet having a porosity between 20 and 40%, wherein said pharmaceutical composition contains water-soluble saccharides by not lower than 30%.

* * * * *